(12) United States Patent
Chung et al.

(10) Patent No.: US 8,748,445 B2
(45) Date of Patent: Jun. 10, 2014

(54) METHODS FOR TREATING GLIOMA

(75) Inventors: W. Joon Chung, Birmingham, AL (US); Harald Sontheimer, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 1264 days.

(21) Appl. No.: 11/791,588

(22) PCT Filed: Oct. 27, 2005

(86) PCT No.: PCT/US2005/038380
§ 371 (c)(1),
(2), (4) Date: Aug. 7, 2008

(87) PCT Pub. No.: WO2006/049957
PCT Pub. Date: May 11, 2006

(65) Prior Publication Data
US 2009/0117031 A1    May 7, 2009

Related U.S. Application Data

(60) Provisional application No. 60/622,426, filed on Oct. 27, 2004, provisional application No. 60/702,348, filed on Jul. 25, 2005.

(51) Int. Cl.
| | |
|---|---|
| A01N 43/54 | (2006.01) |
| A61K 31/505 | (2006.01) |
| A01N 43/40 | (2006.01) |
| A61K 31/44 | (2006.01) |
| A01N 41/10 | (2006.01) |
| A61K 31/10 | (2006.01) |
| C07D 239/02 | (2006.01) |
| C07D 213/72 | (2006.01) |
| C07D 211/72 | (2006.01) |
| C07D 211/84 | (2006.01) |
| C07C 315/00 | (2006.01) |
| C07C 317/00 | (2006.01) |

(52) U.S. Cl.
USPC ........... 514/275; 514/352; 514/709; 544/297; 546/304; 568/30

(58) Field of Classification Search
USPC ........... 514/275, 352, 709; 544/297; 546/304; 568/30
See application file for complete search history.

(56) References Cited

U.S. PATENT DOCUMENTS 6,197,820 B1 *   3/2001   Sontheimer et al. .......... 514/567

OTHER PUBLICATIONS

Ye et. al., The Journal of Neuroscience, 1999, Society for Neuroscience, vol. 19, No. 24, pp. 10767-10777.*
Chamberlain et. al., Western Journal of Medicine, 1998, California Medical Association, vol. 168, No. 2, pp. 114-120.*
Jendrossek et. al., Expert Opinion Investigational Drugs, 2003, Ashley Pub., vol. 12, No. 12, pp. 1899-1924.*
Judson et. al., Gynecologic Oncology, 2004, Elsevier, vol. 93, pp. 667-670.*
Okuno et. al., British J. Cancer, 2003, Cancer Research UK, vol. 88, pp. 951-956.*
Robe et. al., Clinical Cancer Research, 2004, American Association for Cancer Research, vol. 10, pp. 5595-5603.*
Gossmann et. al., Journal of Magnetic Resonance and Imaging, 2002, Wiley-Liss, vol. 15, pp. 233-240.*
Sarjubhai A. Patel et al., "Differentation of substrate and non-substrate inhibitors of transport system xc: an obligate exchanger of L-glutamate and L-cystine," Neuropharmacology 46 (2004) 273-284, Elsevier Ltd., US.
S. Kato et al., "A Mechanism for Glutamate Toxicity in the C6 Glioma Cells Involving Inhibition of Cystine Uptake Leading to Glutathione Depletion," Neuroscience, 1992, pp. 903-914, vol. 48, No. 4, Pergamon Press Ltd, GB.
PW Gout et al., "Increased cystine uptake capability associated with malignant progression of Nb2 lymphoma cells," Leukemia, 1997, pp. 1329-1337, vol. 11, Stockton Press.
PW Gout et al., "Sulfasalazine, a potent suppressor of lymphoma growth by inhibition of the xc cystine transporter: a new action for an old drug," Leukemia, 2001, pp. 1633-1640, vol. 15, Nature Publishing Group.

* cited by examiner

*Primary Examiner* — Sarah Pihonak
(74) *Attorney, Agent, or Firm* — Thomas G. Peterson; Bradley Arant Boult Cummings LLP

(57) ABSTRACT

The present disclosure provides for method of treatment and/or prevention of disease states that require cystine for maintenance or progression of the disease state. In addition, methods for screening and identifying novel therapeutic agents useful in the treatment of such disease states are described. In one embodiment, the disease state is a cancer, such as, but not limited to, glioma. In this embodiment, methods for the treatment and prevention of glioma by inhibiting cystine uptake or decreasing intracellular cystine concentrations are provided. The present disclosure teaches that glioma cells are dependent on system Xc for cystine uptake. Pharmacological inhibition of system Xc causes a rapid depletion of intracellular glutathione, resulting in decreased cell growth. In contrast, non-malignant astrocytes and cortical neurons remain viable in the presence of Xc inhibitors and continue to take up cystine via alternate amino acid transporters.

13 Claims, 10 Drawing Sheets

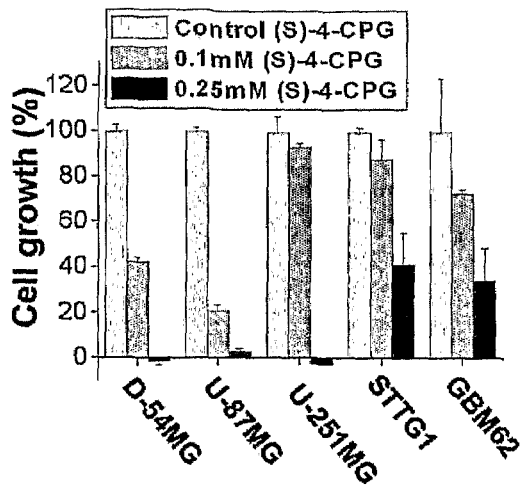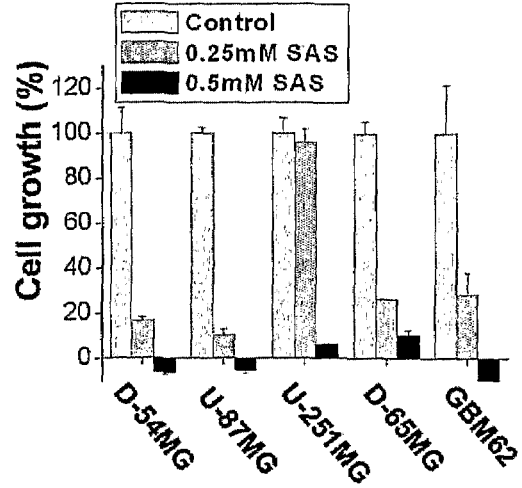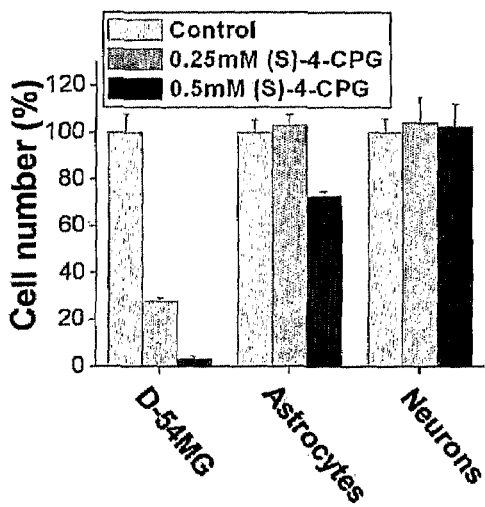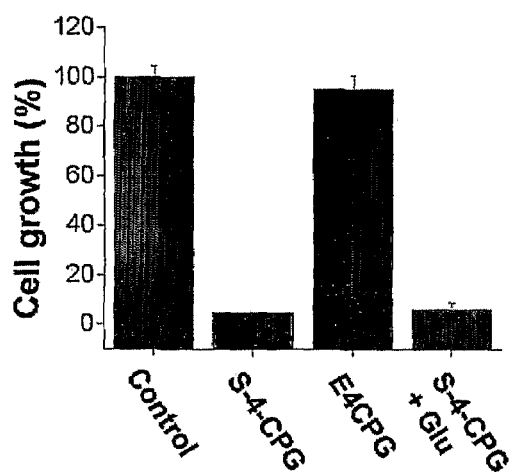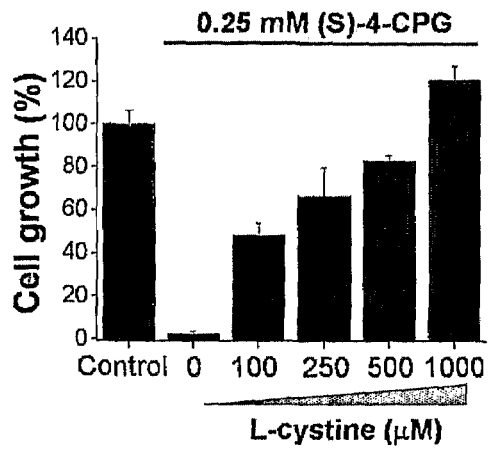

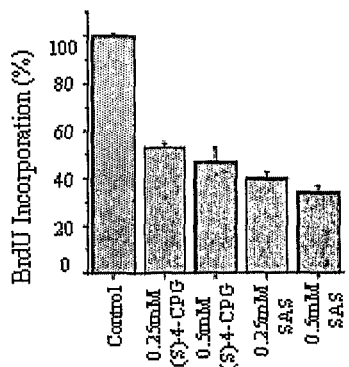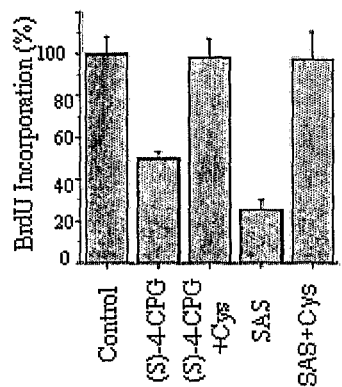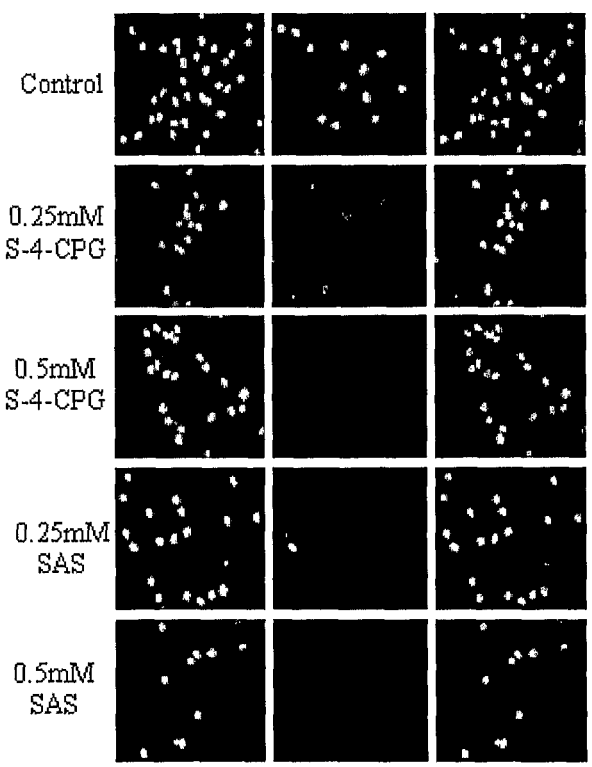

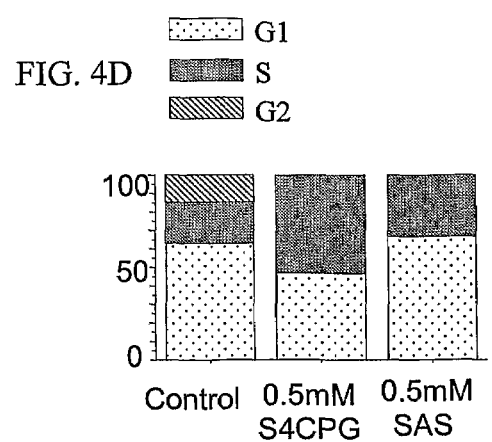

Saline, 30 days

Sulfasalazine, 30 days

METHODS FOR TREATING GLIOMA

The present disclosure claims priority to U.S. provisional patent Nos. 60/622,426 (filed Oct. 27, 2004) and 60/702,348 (filed Jul. 25, 2005), the contents of each being hereby incorporated by reference.

The work described in the present application was supported by National Institute of Health Grants RO1-NS36692 and P50CA97247. The United States government has certain rights in the inventions disclosed herein.

FIELD OF THE DISCLOSURE

The present disclosure relates generally to the treatment and or prevention of a diseases state that required cystine for maintenance of progression of the disease state. More specifically, the present disclosure relates to the treatment and prevention of glioma via the inhibition of cystine uptake, such as via the inhibition of the cystine-glutamate exchanger, system Xc.

BACKGROUND

Transformed cells are known to be more metabolically active than non-transformed cell. This increased metabolic activity is the result of the deregulated growth controls in the transformed cells. Increased metabolic activity has many effects, including, but not limited to, increased reactive oxygen species (ROS) production. If not countered by cellular anti-oxidant defenses, increased production of ROS species can lead to cellular damage, increased mutation rates and even cell death, such as via activation of the apoptotic pathway. Therefore, these transformed cells are dependent on cellular anti-oxidant defenses for survival. As a result of this dependence, if such transformed cells could be deprived of the chemical building blocks required to sustain the anti-oxidant defenses, the growth and/or viability of the transformed cells could be decreased.

Glial-derived tumors (i.e. gliomas) are transformed cells that display increased metabolic activity as a result of the transformation process. Gliomas comprise a diverse group of neoplasms that differ in their morphology, their CNS location, their degree of invasiveness, their tendency for progression, and their growth characteristics. Neoplastic transformation can occur in all glial cell types, thereby producing a large range of pathological and morphological variants. Most primary brain tumors derived from glial cells have lost growth control regulation, giving rise to astrocytomas, glioblastomas, or oligodendrocytomas. High-grade gliomas account for 30% of primary brain tumors in adults, and are the second most common cause of cancer death in children under 15 years of age (13, 14). High-grade gliomas are divided by grade into two categories: anaplastic astrocytomas (WHO Grade III) and glioblastoma multiforme (GBM; WHO Grade IV) (15). There are also two other histopathologically classified grades of brain tumors, namely, Grades I and II. Increasing grades represent increasing malignancy and decreasing differentiation, which is associated with increased mitotic activity and enhanced cell migration (16, 17).

As a result of their increased metabolic activity, glioma cells have been shown to produce large quantities of ROS. In response to this increased production of ROS, glioma cells have been shown to produce increased levels of antioxidants, such as glutathione. Cystine is an essential precursor in the synthesis of glutathione, an important intracellular antioxidant responsible for scavenging ROS (1). It was believed cystine was transported into glioma cells via a variety of cellular pathways, including system Xc. System Xc is a Na+-independent glutamate transport system that has been functionally described for several decades (2). System Xc is highly expressed in glioma cells. System Xc is a heterodimeric protein complex consisting of a catalytic light chain (xCT) that confers substrate specificity and a regulatory heavy chain (4F2hc) (3). Cloning studies have shown that xCT belongs to the family of 12-transmembrane domain amino-acid transporter proteins (3). xXT has been shown to exist in two splice variants, hxCTa and hxCTb, in gliomas. 4F2hc is a cell surface glycoprotein previously known as CD98 that is essential for membrane localization of the transporter (4). Only the heterodimeric protein complex functions as an amino-acid transporter.

Unlike glioma cells, system Xc is not implicated in cystine uptake in mature neurons or astrocytes (7, 8), which use Na+-dependent glutamate transporters for this purpose. Inhibition of cystine uptake by blocking system Xc, which would reduce cellular levels of glutathione and increase the susceptibility of glioma cells to ROS-mediated damage and cell death, would therefore be an effective treatment for gliomas. Importantly, such inhibition of system Xc would not negatively impact the function of non-transformed glial cells since they do not rely on system Xc for cystine uptake.

The prior art has not understood that glioma cells rely almost exclusively on system Xc for the uptake of cystine. As a result, methods for the treatment of glioma cells directed solely at inhibiting system Xc have not been described. Prior art methods utilized treatments that inhibited cystine uptake in non-transformed neural cells, often forcing the co-administration of compounds to address this issue.

The present disclosure describes generally methods for the treatment and prevention of disease states that require cystine for maintenance or progression of the disease state. In addition, methods for screening and identifying novel therapeutic agents useful in the treatment of such disease states are described. In one embodiment, the disease state is a cancer, such as, but not limited to, glioma. More specifically, the present disclosure describes methods for the treatment and prevention of glioma by inhibiting cystine uptake or decreasing intracellular cystine concentrations, thereby inhibiting the ability of glutathione to maintain ROS levels at conditions which are not harmful to the transformed glial cells.

BRIEF DESCRIPTION OF THE FIGURES

FIG. 1A shows that the catalytic subunit, xCT, and the regulatory subunit, 4F2hc, of system Xc are present in all human glioma cell lines tested and the primary glioma culture as determined by RT-PCR and that the regulatory subunit is present as well as determined by Western blot analysis. FIG. 1B shows that the catalytic subunit xCT is present in equal amounts from patient biopsies from non-malignant brain tissue (ID 59, ID 56 and ID 78) and from glioma biopsies (ID 47, ID 34 and ID 20) as determined by RT-PCR. FIG. 1C shows that the expression of GLT-1 (detected by Western blot analysis) is almost completely abolished in tumor biopsies of glioma patients (ID20, ID47, ID34, ID21 and ID25) while being strongly detected in biopsy samples from non-malignant brain tissue (ID61, ID57, ID59 and ID78). The expression of the regulatory subunit, 4F2hc was comparable between all samples.

FIG. 2A shows that co-incubation with 0.25 mM S-4-CPG or sulfasalazine reduces cystine uptake in D-54MG, U-847MG and U-251-MG glioma cell lines, as well as in a primary glioma culture, GBM62. FIG. 2B shows that sulfasalazine impacts cyctine uptake into cortical astrocytes to a significantly lesser degree that in D-54MG glioma cells. FIG. 2C shows that cystine uptake in cortical neurons was negligible in comparison to D-54MG glioma cells and cortical astrocytes. FIG. 2D shows that 50-500 µM sulfasalazine depleted intracellular glutathione concentrations in a time and dose dependent manner in D-54MG glioma cells. FIG. 2E shows that 50-500 µM sulfasalazine had a smaller effect on intracellular glutathione concentrations as compared to glioma cells, FIG. 2F shows that 0.25 mM sulfasalazine and (s)-4-CPG depleted intracellular glutathione concentration in glioma cells (D-54MG, U-87MG and U-251MG) and in a primary glioma culture (GBM64) but not in cortical astrocytes or neurons.

FIGS. 3A-E show that system Xc inhibition by (S)-4-CPG and sulfasalazine blocks glioma cell growth. FIG. 3A shows that treatment of glioma cells (D-54MG, U-87MG, U-251MG and STTS1) and a primary glioma culture (GBM62) with 0.1 mM and 0.25 mM (S)-4-CPG inhibited cell growth in a dose dependent manner. FIG. 3B shows that treatment of glioma cells (D-54MG, U-87MG, U-251MG and STTS1) and a primary glioma culture (GBM62) with 0.25 mM and 0.5 mM sulfasalazine inhibited cell growth in a dose dependent manner. FIG. 3C shows that 0.25 mM and 0.5 mM (S)-4-CPG had negligible impact on the growth of cortical astrocytes and neurons; D-54MG cells exposed to the same (S)-4-CPG concentrations are provided as a comparison. FIG. 3D shows that the broad spectrum mGluR antagonist E4CPG (0.25 mM) does not inhibit cell growth in glioma cells to any significant degree and that treatment with 1 mM glutamate does not reverse the growth inhibiting affects of (S)-4-CPG indicating that the observed growth inhibition is not mediated by mGluRs. FIG. 3E shows that growth inhibition caused by 0.25 mM (S)-4-CPG is reversed in a dose dependent manner by L-cystine (0-1000 µM).

FIGS. 4A-D show that system Xc inhibitors block DNA synthesis and arrests cell cycle progression in glioma cells. FIG. 4A shows that 0.25-0.5 mM (S)-4-CPG and sulfasalazine inhibit BrdU incorporation into chromosomal DNA in D-54MG cells; FIG. 4B shows that the proportion of cells undergoing active DNA synthesis was reduced by the treatment of (S)-4-CPG or sulfasalazine. The nuclei of all cells were visualized by co-staining with the nuclear marker DAPI. FIG. 4C shows cystine reverses DNA synthesis inhibition caused by the treatment with (S)-4-CPG and sulfasalazine. FIG. 4D shows that treatment with 0.5 mM (S)-4-CPG and 0.5 mM sulfasalazine results in the arrest of cells in G1 or S phase. The cells were fixed with para-formaldehyde and stained with propidium iodide after incubation with drugs. The DNA content of each cell was measured by the fluorescence of propidium iodide using flow cytometry.

FIG. 5A shows that treatment with the characterized free radical scavengers vitamin E, TMPO and PBN partially restored glioma cell growth in the presence of (S)-4-CPG. FIG. 5B shows that incubation with the indicated concentration of (S)-4-CPG caused DNA fragmentation characteristic of apoptotic cell death as determined by flow cytometry. FIG. 5C shows that both (S)-4-CPG and sulfasalazine induced activated caspase 3 in D-54MG cells. FIG. 5D shows that the panspecific caspase-3 inhibitor Boc-D-FMK (100 µM) blocked cell death induced by 0.25 mM (S)-4-CPG. FIG. 5E shows that 1 mM sulfasalazine and 0.5 mM (S)-4-CPG induced cell death as determined by FACS analysis using the Live/Dead assay it (Molecular Probes) and that the cell death induced by 0.5 mM (S)-4-CPG could be reversed in the presence of 1 mM cystine.

FIG. 6A shows that co-incubation with glutathione ethyl ester (GSHest), a membrane permeable form of glutathione, prevented sulfasalazine-induced (0.4 mM) intracellular glutathione depletion in D-54MG cells. FIG. 6C shows that glutathione ethyl ester (GSHest) at 1 mM restores growth of D-54MG cells from sulfasalazine (0.4 mM) and (S)-4-CPG (0.4 mM) induced growth inhibition.

FIG. 7A shows that sulfasalazine slows tumor growth in CB-17 scid mice bearing experimental brain tumors creating by xenografting D-54MG cells stably expressing the luciferase gene into the cranium of the mice. Control group animals received 1 ml of saline intraperitoneally twice dailt and the two test groups received 8 mg sulfasalazine (in 1 ml saline) twice daily for either 1 or 3 weeks. Subject mice were retreated at day 53 for 3 days to evaluate the continuing responsiveness to treatment. FIG. 7B shows that sulfasalazine slows tumor growth in CB-17 scid mice bearing experimental brain tumors creating by xenografting D-54MG cells stably expressing the luciferase gene into the cranium of the mice. Control group animals received 1 ml of saline intraperitoneally twice dailt and the two test groups received 8 mg sulfasalazine (in 1 ml saline) twice daily for 3 weeks followed by one daily dose thereafter. FIGS. 7C and 7D show representative hematoxylin-eosin staining of mouse brain sections obtained from control, saline treated animals (FIG. 7C) or sulfalsalazine treated animals (FIG. 7D); images are shown at 1.25× magnification.

FIGS. 8A and 8B show, respectively, shows sections of mouse brain from control saline treated animals (subject was at 50 days survival) and sulfasalazine treated animals (subject was at 56 days survival with treatment being as described in FIG. 7A) using the ApopTag kit at 20× magnification. The brown areas indicate areas of necrosis. The slides were counterstained using hematoxyline-eosin staining. FIGS. 8C and 8D, respectively, show representative examples of TUNEL staining on the samples described in FIGS. 8A and 8B at 40× magnification. FIGS. 8E and 8F, respectively, show representative examples of Ki-67 immunohistochemistry on the samples described in FIGS. 8A and 8B at 20× magnification. GLT-1 antibody is shown in green with Ki-67 positive cells shown in red; DAPI staied nuclei are blue.

DETAILED DESCRIPTION

Definitions

Figure 1A:
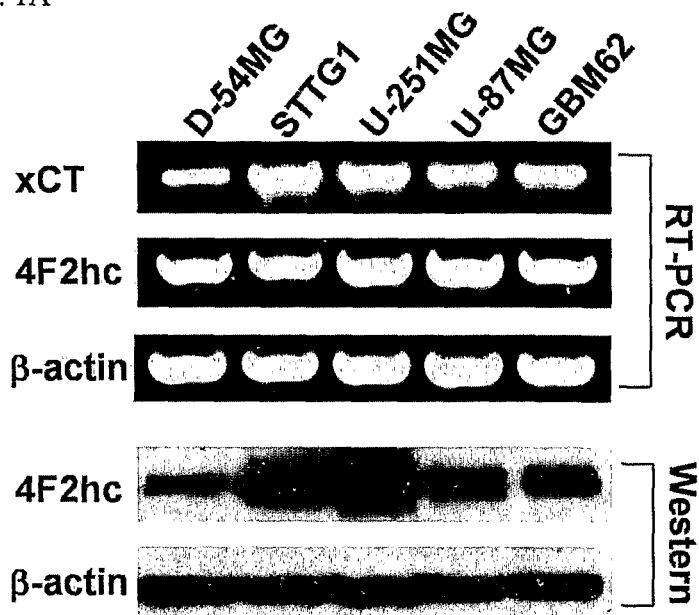
FIGS. 1A-C show the expression of the cystine-glutamate exchanger, system Xc, in glioma cell lines (D-54MG, STTG1, U-251MG, and U-87MG) as well as in a primary glioma culture, GBM62.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "prevent", "preventing", "prevention" "suppress", "suppressing" and suppression as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be useful.

The terms "treat", "treating" and "treatment" as used herein refers to administering a compound either alone or as contained in a pharmaceutical composition after the onset of clinical symptoms of a disease state so as to reduce or eliminate any symptom, aspect or characteristic of the disease state. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, and may include the knowledge that the patient is ill as the result of a disease state that is treatable by a compound or pharmaceutical composition of the disclosure.

The term "in need of prevention" as used herein refers to a judgment made by a caregiver that a patient requires or will benefit from prevention. This judgment is made based on a variety of factors that are in the realm of a caregiver's expertise, and may include the knowledge that the patient may become ill as the result of a disease state that is treatable by a compound or pharmaceutical composition of the disclosure.

The term "individual" or "patient" as used herein refers to any animal, including mammals, such as, but not limited to, mice, rats, other rodents, rabbits, dogs, cats, swine, cattle, sheep, horses, or primates, or humans. The term may specify male or female or both, or exclude male or female.

The term "therapeutically effective amount", in reference to the treating, preventing or suppressing of a disease state, refers to an amount of a compound either alone or as contained in a pharmaceutical composition that is capable of having any detectable, positive effect on any symptom, aspect, or characteristics of the disease state/condition. Such effect need not be absolute to be beneficial.

General

Cystine is required to sustain cellular protein biosynthesis and the production of antioxidants, such as, glutathione. Compared to non-transformed cells, transformed cells, such as glioma cells, require a more substantial cystine uptake to sustain the enhanced growth and the associated higher metabolic rates (11). Moreover, enhanced metabolic activity leads to the enhanced generation of reactive oxygen species (ROS), which, if uncontrolled, can damage cellular membranes, decrease energy metabolism and cause mutations in DNA. Cells may avoid damage by ROS through enhanced synthesis of antioxidants, such as glutathione. Enhanced synthesis of glutathione has been documented in snap-frozen samples of human glioma biopsies (12).

The present disclosure describes methods for the treatment and/or prevention of a disease state that depends on the enhanced uptake of cystine for the maintenance and/or progression of the disease state. The enhanced cystine uptake is used for the enhanced production of antioxidants, such as glutathione. The present disclosure teaches that by blocking the enhanced uptake of cystine, such as through the inhibition of system, Xc, cellular antioxidant defense may be compromised. Therefore, such methods offer novel and effective methods of treatment and/or prevention for such disease states. The present disclosure utilizes Glial derived tumor cells as an illustrative embodiment of this principle. However, the teachings of the present disclosure may be applied to other cell types that rely on enhanced cystine uptake and the illustrative description of glioma cells in the present disclosure is not meant to limit the teachings of the present disclosure to glioma cells.

The present disclosure describes the dependence of glial-derived tumor cells upon cystine uptake via system Xc in order to maintain glutathione at concentrations required to combat the increased levels of ROS and to support cell growth/viability. Such glioma cells are referred to as Xc-dependent glioma cells. Xc dependent glioma cells are defined as cells that rely on system Xc to provide cystine levels sufficient for the production of glutathione levels required to maintain glioma cell viability. In one embodiment, Xc dependent gliomas rely on system Xc for 95-100% of the total cystine taken up by said glioma cells. In an alternate embodiment, Xc dependent gliomas rely on system Xc for 85-95% of the total cystine taken up by said glioma cells.

High levels of both the catalytic and regulatory subunit of system Xc are expressed in glioma cells from patient biopsies and in established glioma cell lines. The present disclosure shows that system Xc represents the only viable pathway for cystine uptake in glioma cells, a fact which was not heretofore appreciated in the art, and that the inhibition of system Xc leads to selective, apoptotic, caspase-mediated cell death of glioma cells. However, other glial cells, such as astrocytes and neurons, rely on other mechanisms for cystine uptake (such as Na+-dependent cystine transport pathways, such as GLT-1) and are not impacted by inhibition of system Xc. Therefore, inhibition of cystine uptake serves as a point for pharmacological intervention in the treatment of gliomas. Methods for treating gliomas by inhibiting cystine uptake via system Xc are described. In addition, methods for screening and identifying novel therapeutic agents useful in the treatment of gliomas by inhibiting cystine uptake via system Xc are described.

As described in the present disclosure, system Xc was expressed in glioma cells obtained from brain biopsies of patients diagnosed with GBM and in all of the established glioma cell lines examined. The Na+-dependent glutamate transporter GLT-1, that can also transport cysteine, which is the oxidized form of cystine, was not expressed in these glioma cells. Therefore, these glioma cells depended exclusively on system Xc for cystine uptake. Inhibiting this cystine uptake by inhibiting the system Xc transporter caused a dose-dependent reduction in glioma cell growth (in both glioma cells obtained from patient biopsies and in established glioma cell lines). Neither astrocytes nor neurons share such an exclusive dependence and hence their growth was not impeded when system Xc was inhibited. Astrocytes and neurons were able to continue their production of glutathione after system Xc was inhibited whereas gliomas showed near complete glutathione depletion following a 48 hour block of system Xc. This indicates that neurons and astrocytes either express additional amino-acid transporters that can also transport cysteine (the oxidized form of cystine) or that they use other pathways for antioxidant synthesis. In neurons and astrocytes, the Na+-dependent EAAT family of transporters are abundantly expressed (18) and have been shown to transport cystine (7, 19). In brain synaptosomes Na+dependent cystine transport accounts for 90% of cystine uptake (19) and for about 80% in cultured astrocytes (8). In line with previous work (20), the present disclosure shows that the EAAT transporter GLT-1 was lost from the membrane of glioma cells, thus leaving no back-up system for cystine transport.

The potential advantage of using system Xc inhibitors, in contrast to pharmaceutical agents that directly inhibit glutathione synthesis, is that glutathione synthesis would not be impaired in other cell types, notably liver cells and other glial cells. A variety of inhibitors of system Xc have been described. These include phenyl glycine derivatives, such as, but not limited to (S)-4-carboxyphenylglycine, (S)-4CPG, and the N-heterocyclic substituted salicylate compounds, such as, but not limited to, sulfasalazine, disalazine, and salazosulfadimnidine. Sulfasalazine is available under the brand name Azulfidine (Pharmacia/Upjohn). A structural analogue of sulfasalazine known by the brand name Susalimod is available in an injectable form. Preliminary data suggest that in the brain, the phenyl glycine derivatives and salicylates are well tolerated by neurons and astrocytes. The present disclosure is not dependent on a particular inhibitor of system Xc. Any system Xc inhibitor currently known in the art, or discovered in the future, has utility in the treatment methods described herein. Exemplary system Xc inhibitors are described in U.S. patent application Ser. No. 10/258,459 and U.S. Pat. No. 6,521,640, which are hereby incorporated by reference.

Pharmaceutical Compositions, Modes of Administration and Methods of Treatment

The present disclosure provides methods for the treatment and/or prevention of a disease state that that requires cystine for maintenance and/or progression of the disease state. In one embodiment, the disease state may depend on system Xc for the uptake of cystine. In one embodiment, the disease state is a cancer, such as but not limited to a glioma. The present disclosure provides exemplary compounds that may be used in the methods of treatment and prevention described herein. In addition, the present disclosure provides for methods to identify additional compounds that may be used in the treatment and/or prevention methods described herein. The compound used in the treatment and/or prevention may be provided alone or as a part of a pharmaceutical composition comprising a pharmaceutically acceptable carrier and other ingredients known in the art. The pharmaceutically acceptable carriers described herein, include, but are not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds and pharmaceutical compositions can be administered by any conventional method available for use in conjunction with pharmaceuticals, either as individual therapeutic agents or in combination with additional therapeutic agents. The compounds and pharmaceutical compositions are administered in therapeutically effective amount. The therapeutically effective amount and the dosage of the compound or pharmaceutical composition administered will, of course, vary depending upon known factors, such as the pharmacodynamic characteristics; the mode and route of administration; the age, health and weight of the subject; the severity and stage of the disease state; the kind of concurrent treatment; the frequency of treatment; and the effect desired. The total amount of the compound (i.e. active ingredient) administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

A daily dosage of active ingredient can be expected to be about 0.001 to 1000 milligrams (mg) per kilogram (kg) of body weight. In one embodiment, the total amount is between about 0.1 mg/kg and about 1000 mg/kg of body weight; in an alternate embodiment between about 1.1 mg/kg and about 100 mg/kg of body weight; in yet another alternate embodiment between 0.1 mg/kg and about 30 mg/kg of body weight. The above described amounts may be administered as a series of smaller doses over a period of time if desired. As would be obvious, the dosage of active ingredient may be given other than daily if desired.

Dosage forms of the pharmaceutical compositions described herein (forms of the pharmaceutical compositions suitable for administration) may contain from about 0.1 mg to about 500 mg of active ingredient per unit. In these pharmaceutical compositions, the active ingredient will ordinarily be present in an amount of about 0.5-95% weight based on the total weight of the composition. Multiple dosage forms may be administered as part of a single treatment.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can consist of (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Forms of systemic administration of the pharmaceutical compositions include injection and infusion. Such injection and infusion routes, include, but are not limited to, subcutaneous, intramuscular, intracranial and intraperitoneal. Alternative means for systemic administration include transmucosal and transdermal administration using penetrants such as bile salts or fusidic acids or other detergents.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Methods of Treatment and Prevention

In one embodiment, the teachings of the present disclosure provide for the use of such compounds and pharmaceutical compositions in a method of treating a disease state that that requires cystine for maintenance of progression of the disease state. In one embodiment, the treatment inhibits the cellular uptake or concentration of cystine or a product of cystine, such as but not limited to an antioxidant compound (for example glutathione). Such inhibition need not be complete to be useful. The method of treatment comprises the steps of: (i) identifying a patient in need of such treatment; (ii) providing a compound or pharmaceutical composition containing at least one compound that inhibits the cellular uptake or concentration of cystine; and (iii) administering such compounds or pharmaceutical composition in a therapeutically effective amount to a patient in need of such treatment.

In one embodiment, the teachings of the present disclosure provide for the use of such compounds and pharmaceutical compositions in a method of preventing or suppressing a disease state that that requires cystine for maintenance of progression of the disease state. Such inhibition need not be complete to be useful. The method of preventing or suppressing comprises the steps of: (i) identifying a patient in need of such prevention; providing a compound or pharmaceutical composition containing at least one compound that inhibits the cellular uptake or concentration of cystine; and (iii) administering such compounds or pharmaceutical composition in a therapeutically effective amount to a patient in need of such prevention.

In one specific embodiment, the disease state in the methods of treatment and prevention is glioma. Therefore, the present disclosure provides for methods for the treatment and prevention of glioma by inhibiting the uptake of cystine in glioma cells. In one embodiment, the inhibition of cystine uptake is the result of inhibiting system Xc. The inhibition may be a direct inhibition of cystine uptake. In one embodiment, the direct inhibition occurs by blocking the activity of a component of the system Xc antiporter mediating the cystine transport. The inhibition may also be an indirect inhibition. In one embodiment, such indirect inhibition may occur by blocking a signal required for the activity, processing or localization of one or more components of the system Xc antiporter.

The methods of treatment and prevention may also be used in combination with known anti-glioma therapies. In the case of glioma, the method of treatment and prevention may administration of additional anti-glioma compounds and radiation therapy. In one embodiment, the compounds and pharmaceutical compositions described herein are combined with drugs and therapies that lead to increased oxidative stress in the glioma cells. One class of drugs which leads to increased oxidative stress in glioma cells is the alkylating agents. Suitable alkylating agents include, but are not limited to, Lomustine, Carmustine, Streptozocin, Mechlorethamine, Melphalan, Uracil Nitrogen Mustard, Chlorambucil, Cyclophosphamide, Iphosphamide, Cisplatin, Carboplatin, Mitomycin, Thiotepa, Dacarbazin, Procarbazine, Hexamethyl Melamine, Triethylene Melamine, Busulfan, Pipobroman and Mitotane. Radiation therapy also leads to increased production of ROS. As discussed above, cells exposed to the compounds or pharmaceutical compositions of the disclosure have decreased levels of cellular antioxidants, such as glutathione. The increase in ROS produced by drugs (such as alkylating agents) and therapies (such as radiation therapy) may lead to increased cell death in glioma cells due to their inability to inactivate the ROS. For example, the combination of sulfasalazine and Carmustine (BCNU) showed synergistic effects when added in combination. The non-glioma cells will be able to combat the increase in ROS production since their antioxidant defenses are not substantially compromised by the administration of system Xc inhibitors.

Such co-administration may improve the effectiveness of the compounds and pharmaceutical compositions and the methods of treatment and prevention disclosed herein. Furthermore, such co-administration of the compounds and pharmaceutical compositions disclosed herein may improve the effectiveness of the known anti-glioma therapies. For example, administration of the compounds and pharmaceutical compositions of the present disclosure may improve the effectiveness of a radiation therapy. The pharmaceutical compositions disclosed may be formulated to deliver both a compound that inhibits cystine uptake and the additional anti-glioma compound. Alternatively, pharmaceutical compositions containing each of the compounds may be administered separately, either at the same time or sequentially.

In another embodiment, the teachings of the present disclosure provide for the use of such compounds and pharmaceutical compositions in a method of inducing cell death in a cell that is dependent on the uptake of cystine for viability. The cell may be a malignant cell, such as a glioma. The cell may reside in a subject, such as a human subject. In one embodiment, the method of inducing cell death comprises inhibiting the cellular uptake or concentration of cystine or a product of cystine, such as but not limited to an antioxidant compound (for example glutathione). Such inducing need not be complete to be useful. The method of inducing cell death comprises the steps of: (i) providing a compound or pharmaceutical composition containing at least one compound that inhibits the cellular uptake or concentration of cystine; and (iii) contacting such compounds or pharmaceutical composition in a therapeutically effective amount to said cell.

In still another approach, expression of the gene encoding a subunit of system Xc can be inhibited using expression blocking techniques. Known techniques involve the use of antisense sequences and microRNA techniques, either internally generated or separately administered. See, for example, O'Connor, J Neurochem (1991) 56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al., Nucleic Acids Res (1979) 6:3073; Cooney et al., Science (1988) 241:456; Dervan et al., Science (1991) 251:1360. These oligomers can be administered per se or the relevant oligomers can be expressed in vivo.

Methods for Screening

In another embodiment of the present invention, there is provided a method for identifying compounds that inhibit cystine uptake via system Xc, comprising contacting Xc dependent glioma cells with a candidate system Xc inhibitor and determining the inhibition of cystine uptake or determining the activity of the system Xc antiporter. The reduction in the amount of cystine uptake can be determined in one embodiment by direct measurements of cystine or cysteine, or in an alternate embodiment by measurement of products comprising cysteine, such as, glutathione. The method of measuring the amount of products resulting from cystine uptake may be accomplished in one embodiment by detection of a label directly or indirectly associated with said candidate compound or said cystine being taken up by the glioma cell, such as, but not limited to a radiolabel, a fluorescent label and an enzymatic label. In an alternate embodiment, products resulting from cystine uptake may be measured by competition with a labeled competitor and detecting said labeled competitor.

In a further embodiment of the present invention, there is provided a method for identifying potential agents that inhibit cystine uptake via system Xc, comprising contacting Xc dependent glioma cells with an agent that binds directly or indirectly to system Xc subunits, such as, the catalytic subunit, xCT, and the regulatory subunit, 4F2hc, and determining the inhibition of cystine uptake or determining the activity of the system Xc antiporter. In one embodiment, the agent may be an antibody. The antibody may be monoclonal or polyclonal, or any fragment thereof capable of binding, such as, but not limited to Fab2 fragments. The antibody may be specific for said component. In an alternate embodiment, the agent may be a polypeptide capable of inhibiting system Xc. In still a further embodiment, the agent may be a small molecule pharmaceutical capable of inhibiting system Xc. The agent may further comprise a detection molecule. Such detection molecules are well known in the art and may be a radiolabel, a fluorescent label or an enzymatic label.

In one embodiment, such identification involves a screening assay utilizing a system which incorporates the system Xc antiporter in a functional state. A functional state is defined as any system Xc antiporter comprising a combination of subunits resulting in exchange of glutamate for cystine. The screening assay may utilize oocytes, lipid bilayers, mammalian, drosophila, bacterial or yeast cells comprising one or more component of system Xc in a functional state. Furthermore, membrane preparations or vesicles can be formed from any of the above and used to conduct the identification procedures. In addition, the functional state may include certain mutations to subunits of system Xc.

The following examples are given for the purpose of illustrating various embodiments of the invention and are not meant to limit the present invention in any fashion:

EXAMPLES

Example 1

System Xc is Highly Expressed in Human Glioma Cells

Previous studies provide evidence for the unusual release of excitotoxic concentrations of glutamate from gliomas cell lines (10) that lack expression of functional Na+-dependent glutamate transporters (20). Tracer studies suggested that glutamate was released in exchange for cystine being taken up by the glioma cell lines. One candidate system for this glutamate-cystine exchange is system Xc. A combination of RT-PCR and Western blots was used to examine expression of RNA and protein in established and frequently used glioma cell lines (D-54MG, STTG1, U-251MG and U-87MG) and in acute patient-derived tumor biopsies (labeled ID). Representative data from this experiment is summarized in FIG. 1.

Figure 1B:
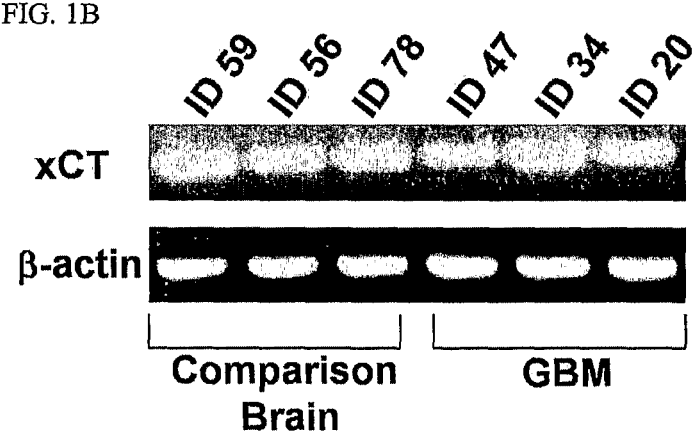
Figure 1C:
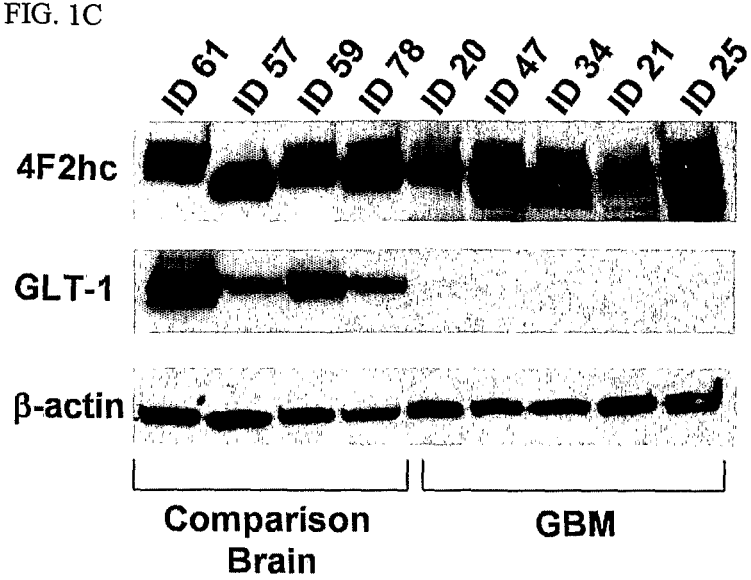

Xc is a hetero-dimeric transporter composed of the catalytic subunit xCT and a regulatory subunit 4F2hc. FIG. 1A shows that RNA transcripts of both the catalytic and the regulatory subunit of system Xc were abundant in all four glioma cell lines (D-54MG, STTG1, U-251MG, and U-87MG) as well as a primary glioma culture (GBM62) examined by RT-PCR. FIG. 1B shows prominent expression of xCT in biopsies from gliomas patients and in control biopsies obtained from non-malignant brain tissue. These studies used primers that recognize both the hxCTa and hxCTb splice variants of the gene. FIG. 1C shows the presence of the obligatory regulatory subunit 4F2hc at the protein level by Western blot analysis in brain tissue biopsies from normal healthy control patients (ID61, ID57, ID59 and ID78) and patients with glioma (ID20, ID47, ID34, ID21 and ID25). Prominent expression of 4F2hc was observed in all biopsies samples examined. Since specific antibodies for xCT are not currently available, the expression of this subunit was not examined by Western blot. FIG. 1C also shows that the Na+-dependent glutamate transporter GLT-1 is prominently expressed in non-malignant human brain samples (ID61, ID57, ID59 and ID78) but was absent in all glioma biopsy samples examined (ID20, ID47, ID34, ID21 and ID25). This indicates that glioma cells lack a common alternate mechanism for the uptake of cystine found in normal brain tissue and relies essentially completely on system Xc for cystine uptake.

Example 2

Figure 2A:
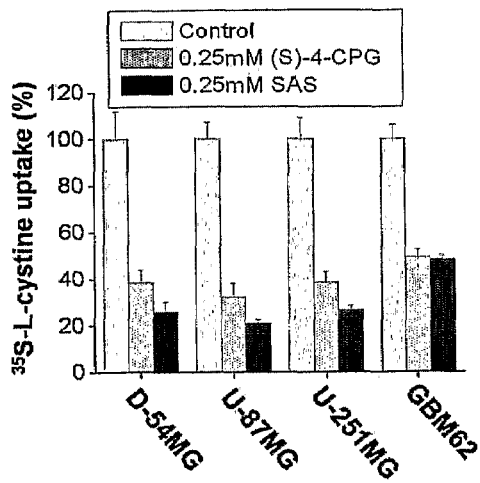
FIGS. 2A-F and B show that inhibitors of system Xc, S-4-CPG and sulfasalazine (SAS), reduce cystine uptake and consequently deplete intracellular glutathione in glioma cells, but not in cortical astrocytes or neurons.
Figure 2B:
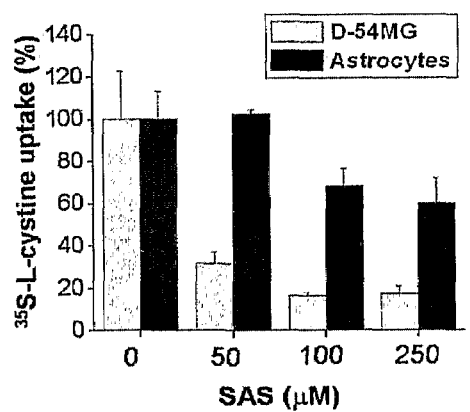
Figure 2C:
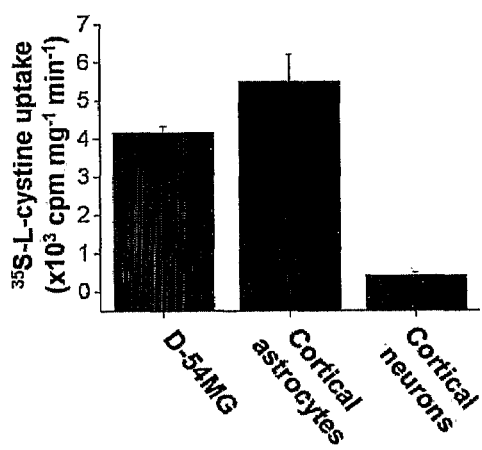

Inhibition of System Xc Reduces Cystine Uptake and Subsequently Depletes Intracellular Glutathione System Xc is a glutamate-cystine exchanger and can therefore be inhibited if the outward directed gradient for glutamate is eliminated by exposure to high concentrations of extracellular glutamate. The principal hypothesis in this study is that system Xc serves as a pipeline for cellular cystine uptake, with glutamate release being an obligatory by-product. Cystine uptake is the rate-limiting step for the synthesis of GSH, which is the main intracellular antioxidant that protects cells from oxidative stress and resulting reactive oxygen species (ROS) (Jefferies et al., 2003). To examine this hypothesis, $^{35}$S-labeled cystine was used to determine the intracellular cystine concentrations in the presence and absence of (S)-4-carboxyphenylglycine [(s)-4-CPG] and sulfasalazine, two potent and relatively selective competitive inhibitors of system Xc. Both drugs reduced $^{35}$S-labeled cystine uptake by 60-80% in glioma lines (d-54MG, U-87MG and U-251MG) and a primary glioma culture (GBM62) (FIG. 2A). This level of inhibition was comparable with the competitive inhibition of this antiporter through impairment of the glutamate gradient by 5 mM L glutamate (data not shown). Pharmacological inhibition of cystine uptake was specific for glioma cells, as sulfasalazine (50-250 mM) exerted only a limited inhibition of cystine uptake in cortical astrocytes (FIG. 2B). Moreover, cystine uptake into cortical neurons (FIG. 2c) was negligible, a finding in agreement with a report showing that neurons preferentially take up cysteine rather than cystine for glutathione biosynthesis.

Figure 2D:
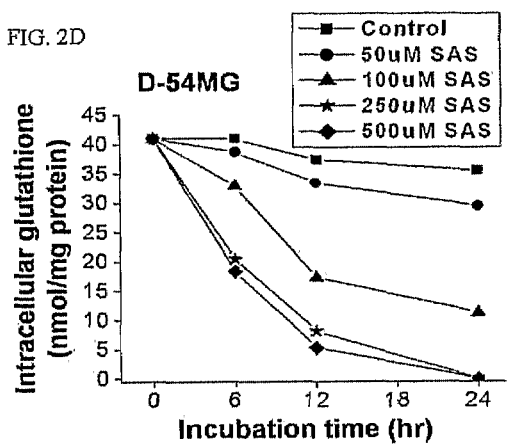
Figure 2E:
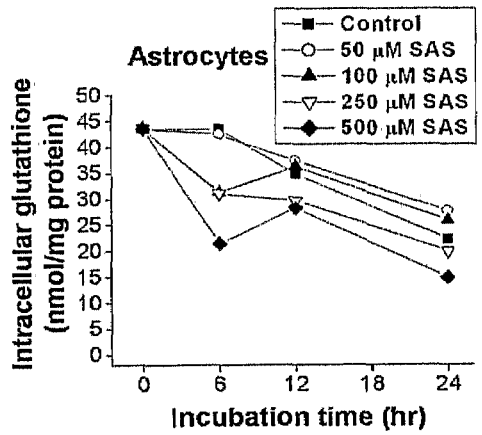
Figure 2F:
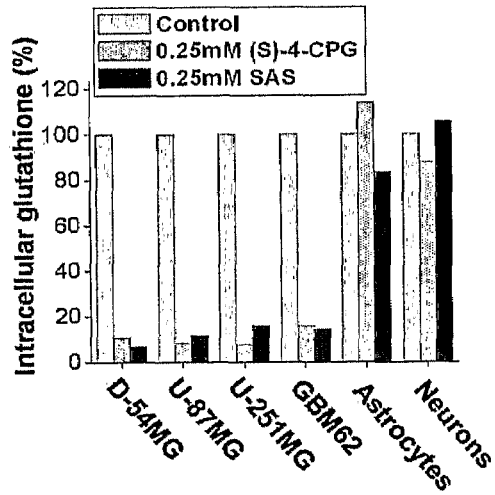

To determine if limiting cystine uptake via system Xc reduces the total intracellular glutathione content (GSH and glutathione disulfide), intracellular glutathione concentrations were determined in the presence and absence of sulfasalazine. Sulfasalazine reduced intracellular glutathione concentration in D-54MG glioma cells in a time and dose-dependent manner with almost complete glutathione depletion after 24 h (FIG. 2D). Similar results were obtained with 0.5 mM (S)-4-CPG (data not shown). This depletion of intracellular glutathione by system Xc inhibitors was observed in all glioma cells examined; however, system Xc inhibitors had only a small effect on astrocytes (FIG. 2E) and did not significantly reduce intracellular glutathione in neurons (FIG. 2F). These results show that system Xc plays an important and essential role in cellular cystine uptake required for the synthesis of intracellular glutathione in glioma cells but not in astrocytes or neurons.

Example 3

Inhibition of Cystine Uptake Via System Xc Leads to Growth Inhibition of Glioma Cells A significant body of literature (for review, see Jefferies et al., 2003) suggests a correlation between glutathione redox status and cell growth whereby reduced glutathione levels slow cell growth. To examine whether the depletion of glutathione via inhibition of cystine uptake by system Xc affects the growth of glioma cells, growth curves for 4 glioma cell lines (D-54MG, U-87MG, U-251MG and STTG1) and a primary glioma culture (GBM62) were established. Cells were grown for 5 days in appropriate cell culture media under standard conditions in the presence of (S)-4-CPG or sulfasalazine each at their most effective glutathione-depleting concentrations (0.1 and 0.25 mM for (S)-4-CPG) and 0.25 and 0.5 mM for sulfasalazine). Both drugs caused dose-dependent growth inhibitions in all the glioma cell lines tested and in the primary glioma culture (FIGS. 3A and 3B). Relative growth stagnated or declined over the 5 day period, indicating that some cell death occurred (negative values in FIGS. 3A and 3B). Neither (S)-4-CPG (FIG. 3C) nor sulfasalazine (data not shown) affected the growth of primary astrocyte cultures or the survival of cortical neuronal cultures, consistent with the above finding that neither drug compromised glutathione status in these cells (FIGS. 2E and 2F).

(S)-4-CPG is frequently used as antagonist for type I metabotropic glutamate receptors (mGluRs), and hence the growth inhibitory effects of (s)-4-CPG could have been mediated by mGluRs. However, this was ruled out as the broad spectrum mGluR antagonist ethyl-4-carboxyphenylglycine (E4CPG) (250 µM) did not inhibit glioma cell growth (FIG. 3D), and 1 mM glutamate failed to overcome the inhibitory effect of 0.25 mM (S)-4-CPG (FIG. 3D). If the inhibitory effects of (S)-4-CPG on cell growth were solely attributable to inhibition of cystine import via system Xc, cell growth should be rescued if cystine levels are experimentally restored. In the presence of 0.25 mM (S)-4-CPG, growth of D-54MG cells indeed recovered by the addition of fourfold excess of cystine (FIG. 3E), but not with glutamate (FIG. 3D), the second substrate for system Xc. As would be expected from a competitive inhibitor, cystine addition exhibited a dose-dependent recovery of cell growth in the presence of a fixed (S)-4-CPG concentration (FIG. 3E). Hence, inhibition of cystine uptake via Xc appears to be the primary effect for (S)-4-CPG.

Example 4

The Growth Inhibition by System Xc Inhibitors is Due to Blocking DNA Synthesis and Arrest of Cell Cycle Progression Inhibition of DNA synthesis was demonstrated by a reduction in BrdU incorporation in D-54MG glioma cells following treatment with (S)-4-CPG and sulfasalazine. BrdU incorporation was measured using an ELISA-based assay. D-54MG cells were grown in the presence or absence of inhibitors for 24 hours and pulsed for 2 hours with BrdU. The cells were cultured for an additional 48 hours and the amount of incorporated BrdU was measured using alkaline phosphatase conjugated to anti-BrdU antibodies. FIG. 4A shows that treatment with 0.25 mM (S)-4-CPG reduced incorporation of BrdU into chromosomal DNA by 50% within 48 hours, with a somewhat larger reduction with 0.5 mM (S)-4-CPG. Sulfasalazine showed a similar reduction of BrdU incorporation (FIG. 4A). The inhibition of DNA synthesis was also seen in immunocytochemical studies. FIG. 4B shows D-54MG glioma cells labeled with the nuclear marker, DAPI. Treatment with (S)-4-CPG or sulfasalazine virtually abolished incorporation of BrdU. These data indicate that inhibition of system Xc, with the resulting decrease in cystine uptake, significantly reduces the number of cells in active DNA synthesis.

To test whether inhibition of cystine uptake affects a specific stage of the cell cycle, changes in total DNA content were measured using flow cytometry following treatment with 0.5 mM (S)-4-CPG and 0.5 mM sulfasalazine. Cells were fixed with para-formaldehyde and stained with the nuclear marker propidium iodide after incubation with drugs. FIG. 4D shows changes in total DNA content with treatments of 0.5 mM (S)-4-CPG and 0.5 mM sulfasalazine. Inhibition of cystine uptake resulted in a reduction of cells in G2 phase and an increase in cells in S phase. These results indicate that inhibition of cystine uptake either blocks the transition from the S phase to the G2 phase or it slows down the progression of the cell cycle at S phase. FIG. 4C shows that exogenously applied cystine was able to reverse the inhibition of BrdU incorporation caused by 0.5 mM (S)-4-CPG and 0.5 mM sulfasalazine, demonstrating that these effects were due to limited cystine availability.

Example 5

Prolonged Inhibition of Cystine Uptake Induces Cell Death

Figure 5A:
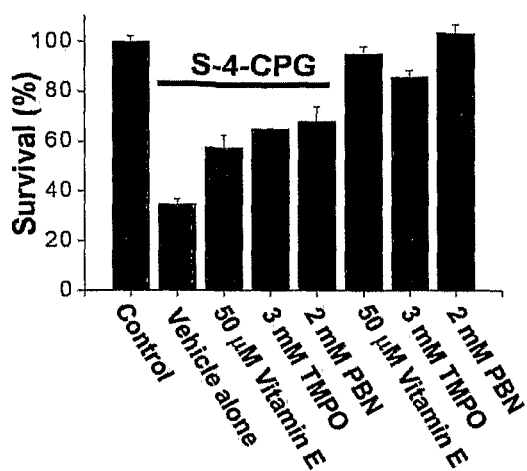
FIGS. 5A-E show that chronic inhibition of cystine uptake induces apoptotic glioma cell death.

Glutathione is one of several antioxidants that cells may use to control ROS generated during normal oxidative metabolism. The observed cell growth inhibition and growth arrest discussed above are likely to impaired antioxidant defenses as a result of decreased cystine uptake. As shown in FIG. 5A, the growth of D-54MG glioma cells was partially restored by treatment with several characterized free radical scavengers including vitamin E, tetramethyl-pyrroline N-oxide (TMPO) ($O_2$-scavenger) and a-phenyl-N-t-butylnitrone (PBN) (OH scavenger).

Figure 5B:
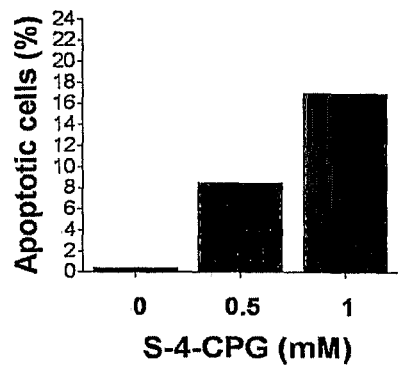
Figure 5C:
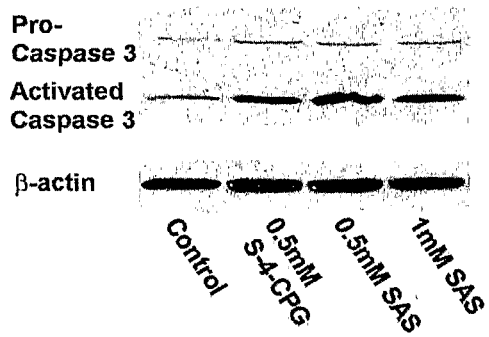
Figure 5D:
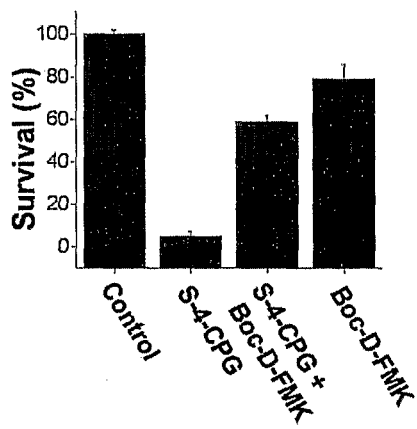
Figure 5E:
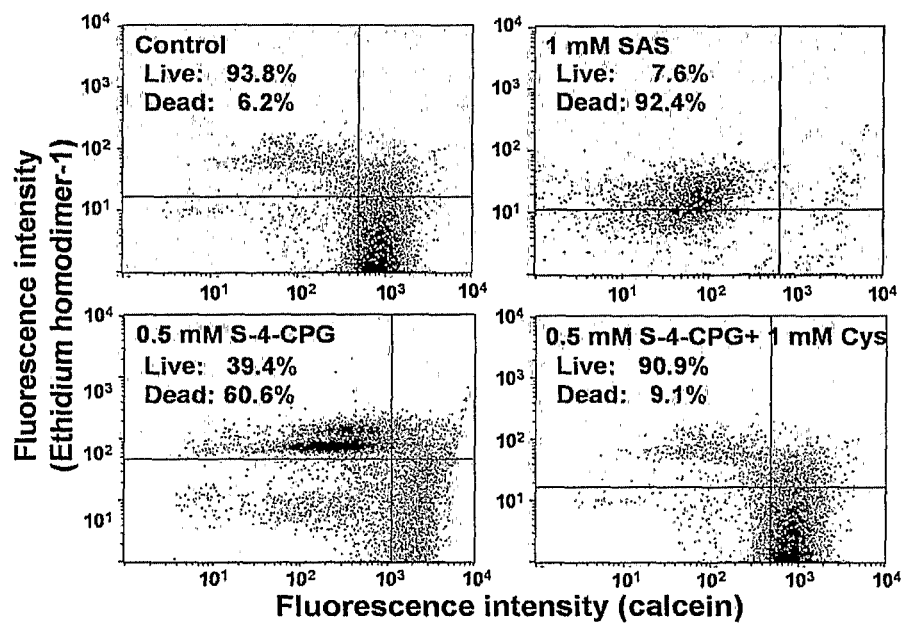

Because an accumulation of ROS can lead to apoptotic cell death, the ability of system Xc inhibitors to induce apoptosis in glioma cells was examined. Exposure of D-54MG glioma cells to 1 mM (S)-4-CPG for 3 days caused 17% of the cell population to be positive for chromosomal DNA fragmentation, a classic manifestation of apoptosis (FIG. 5B). Often apoptosis is dependent on caspase activities, so it was determined whether the system Xc inhibitors induce activated caspase-3, which is the convergent enzyme in the caspase-dependent signaling cascade. Indeed, (S)-4-CPG (0.5 mM) and sulfasalazine (0.5 mM) each increased the activated form of caspase-3 as determined by Western blot analysis (FIG. 5C). As an additional indication that cells underwent the caspase-3-dependent apoptotic cell death, a significant percentage of cells were rescued from cell death induced by (S)-4-CPG (0.25 mM) by the panspecific caspase-3 inhibitor Boc Asp-fluoromethylketone (Boc-D-FMK) (100 µM) (FIG. 5D). These data therefore suggest that cystine depletion via system Xc inhibition increases ROS in glioma cells, which ultimately leads to caspase-mediated apoptotic cell death. Indeed, prolonged treatment of cells with (S)-4-CPG (0.5 mM) or sulfasalazine (1 mM) resulted in apoptotic cell death, as examined by flow cytometry using the Live/Dead assay kit (Molecular Probes) (FIG. 5E). In the continued presence of 0.5 mM (S)-4-CPG over a 5 d period, 60% of glioma cells died (FIG. 5E). With 1 mM sulfasalazine, 90% of cells died over the 5 d incubation (FIG. 5E). Cell death induced by 0.5 mM (S)-4-CPG could be completely prevented if 1 mM cystine was present (FIG. 5E), indicating again that limited cystine availability was the key for cell death induced by these system Xc inhibitors. Similar results were obtained with sulfasalazine (data not shown).

Example 6

Growth Inhibition is Dependent on Intracellular Glutathione Depletion

Figure 6A:
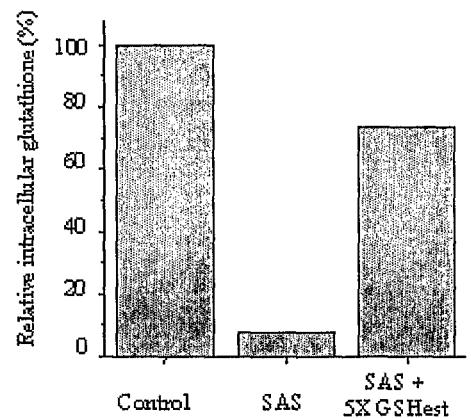
FIGS. 6A and 6B show that inhibition of cell growth by inhibition of system Xc is due to intracellular glutathione depletion.
Figure 6B:
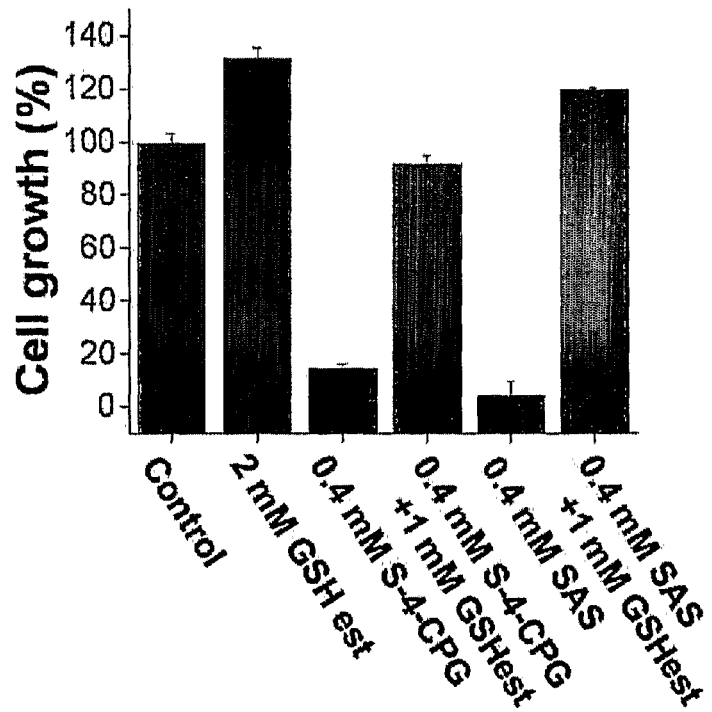

Inhibition of cystine uptake by (S)-4-CPG or sulfasalazine results in intracellular glutathione depletion (FIG. 2D). This intracellular glutathione depletion could be mediated by subsequent depletion of glutathione levels as has been demonstrated in lymphocytes (22) and various tumor cell lines (23, 24, 25) or it could be due to limited protein biosynthesis as seen in CaCO-2 colon cancer cells (26). To further delineate the downstream effects of cystine depletion, we examined whether glutathione ethyl ester (GSHest), a membrane permeable glutathione analog, could rescue cells from the pharmacological inhibition of cystine uptake. Coincubation with glutathione ethyl ester replenished intracellular glutathione levels in sulfasalazine (0.4 mM) treated D-54MG glioma cells (FIG. 6A) and completely restored D-54MG glioma cell growth after treatment with 0.4 mM sulfasalazine or (S)-4-CPG. These effects were identical to the rescue afforded by exogenous cystine (FIG. 3E), whereas L-glutamate failed to restore intracellular glutathione levels (FIG. 3D).

These data indicate that sulfasalazine and (S)-4-CPG-mediated glutathione depletion and inhibition of cell growth is due to a limited supply of cystine, but not glutamate. These data show that intracellular glutathione depletion is sufficient for growth inhibition of glioma cells and is responsible for growth inhibition of glioma cells by system Xc inhibitors.

Example 7

Sulfasalazine Inhibits Tumor Growth In vivo

The above experiments on isolated cells suggest that growth control of actual tumors in vivo might be achieved by inhibiting system Xc as described herein. Therefore, the effect of inhibiting system Xc in an animal model of malignant glioma was examined. In these experiments, both (S)-4-CPG or sulfasalazine were used. Sulfasalazine is a drug that is already clinically used and hence would be a likely candidate for treatment of gliomas in patients. In the described in vivo experiments, human gliomas were xenografted into the cranium of either female CB-17 scid mice or nude mice, both of which are frequently used animal models for malignant gliomas. The intracranial growth of tumors was assessed using the recently developed chemiluminescence methodology for visualizing tumor growth.

Figure 7A:
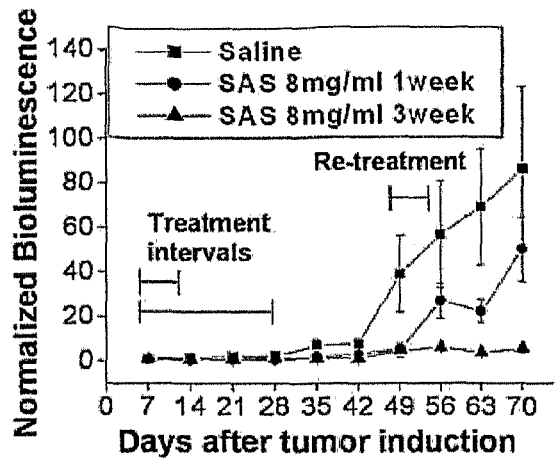
FIGS. 7A-D shows that sulfasalazine retards tumor growth in CB-17 scid and nude mice bearing experimentally-induced brain tumors.

In one set of in vivo experiments, D54-MG glioma cells were stably transfected with the firefly luciferase gene under the control of the CMV promoter. One-half million cells were stereotactically implanted into the cranium of each CB-17 scid mouse. After 7 days, animals were randomized into three groups of 12 animals each. The control group received an intraperitoneal injection of 1 ml dose of saline twice daily. The two test groups received an 8 mg dose of sulfasalazine twice daily for either 1 or 3 weeks. Animals were imaged for tumor size, typically once per week, using a bioluminescence imaging system (IVIS system; Xenogen). Light emission from the tumor regions (in relative photons/second) were quantified using Living Image, version 2.20.1, software provided by Xenogen and plotted as a function of time. The results are shown in FIG. 7A. Control animals (squares) showed rapid tumor expansion, as evidenced by an increase in the relative bioluminescence (i.e., normalized for each animal to its bioluminescence value obtained on day 7 when treatment was initiated). The tumor expansion was significantly reduced in both treatment groups. Importantly, tumor growth resumed to some extent once the treatment was terminated but was again reduced after retreatment with sulfasalazine (FIG. 7A). These data show that intraperitoneal administration of sulfasalazine slows tumor growth in vivo.

Figure 7B:
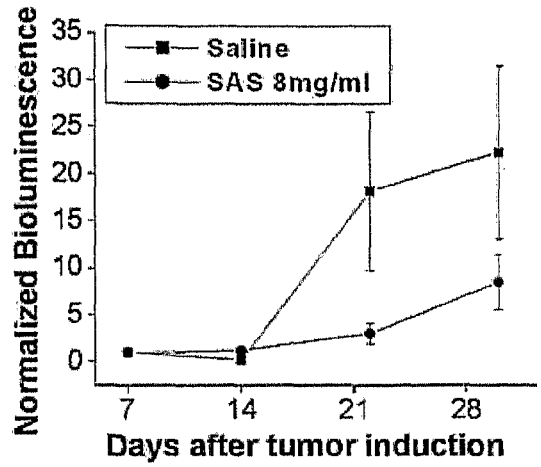

To ensure that these effects were neither cell line specific nor specific to scid mice, the same in vivo experiment was repeated after generating a stable luciferase expressing strain of U87-MG, another frequently used glioma cell line and one for which a similar dependence on system Xc for glutathione synthesis in culture was demonstrated in the present disclosure. These U87-MG cells were similarly implanted intracranially as described above, but this time into CB-17 nude mice. After 7 days, animals were randomized into two groups. The control group received an intraperitoneal injection of 1 ml dose of saline twice daily. The two test groups received an 8 mg dose of sulfasalazine (in 1 ml saline) twice daily for 3 weeks, followed by 1 dose per day of 8 mg sulfasalazine thereafter. Animals were imaged for tumor size, typically once per week, using a bioluminescence imaging system (IVIS system; Xenogen). Light emission from the tumor regions (in relative photons/second) were quantified using Living Image, version 2.20.1, software provided by Xenogen and plotted as a function of time. Bioluminescence data from one of three representative experiments are displayed in FIG. 7B. Once again, sulfasalazine was able to reduce tumor growth significantly as judged by bioluminescence imaging.

Figure 7C:
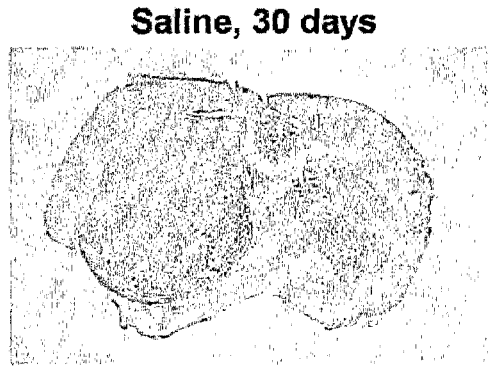
Figure 7D:
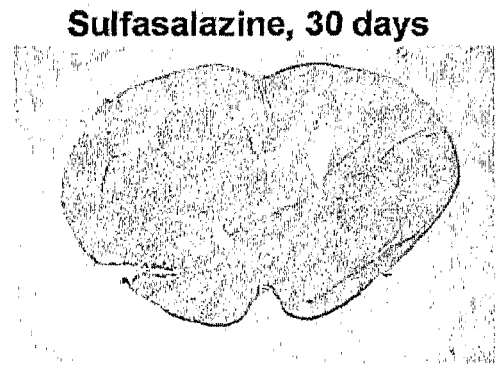

To validate that these experiments represent, at least qualitatively, changes in tumor size, two animals each from the control and treatment groups were sacrificed at 30 days after tumor induction. Histological sections were obtained and traditional hematoxylin-eosin (H&E) staining were performed. FIGS. 7C and 7D show the results for the control group (saline treatment only) and the treatment group (8 mg sulfasalazine in 1 ml saline, twice per day). The tumors in the treatment groups were significantly smaller than in control group, which is consistent with imaging data presented above. As an additional control experiment, it was show that the transfected cells were still expressing luciferase, further validating the results presented above (data not shown).

To assess whether sulfasalazine treatment reduced glutathione levels in the tumor of sulfasalazine-treated animals, monochlorobimane, a fluorescence-based detection kit to quantitatively determine the presence of the reduced form of glutathione (ApoAlert glutathione detection kit; BD Biosciences) (Shih et al., 2003) in both control group and treatment group animals. The control group and treatment group animals were those described in FIG. 7A above. For these experiments, four mice (two control and two treatment) were sacrificed at 44 days after tumor induction, and brains were rapidly frozen and cryosectioned to 20 µM, thawed on ice, and then incubated with 100 µM monochlorobimane for 10 min. Fluorescence intensities were examined using a quantitative fluorescence imaging system comparing side-by-side slices from control group and treatment group animals. In these experiments, 10 slices were examined per animal. Glutathione levels were significantly decreased by treatment with sulfasalazine treatment. After treatment with 8 mg sulfasalazine 2 times per day, glutathione levels decreased approximately 30% (from 100+/−5.6 to 71.7+/−7.5 fluorescence units; p 0.01; t test) in tumors as compared with control animals (receiving saline alone). In parallel studies, the same assay was used on cultured glioma cells to validate these readouts. A 30% decrease in glutathione levels correlates with the glutathione depletion achieved with 70 µM sulfasalazine administered for 24 h to cultured cells; the maximal decrease achieved with 250 µM sulfasalazine in cultured U87-MG cells was 68% (data not shown).

Figure 8A:
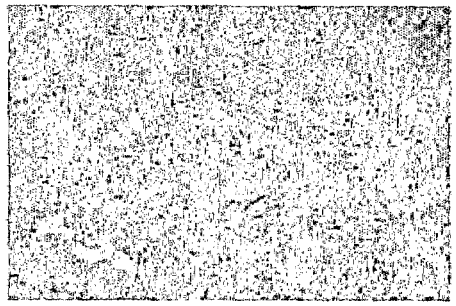
FIGS. 8A-F shows immunohistochemical analysis of the effect of sulfasalazine on in vivo tumors.
Figure 8B:
Figure 8C:
Figure 8D:
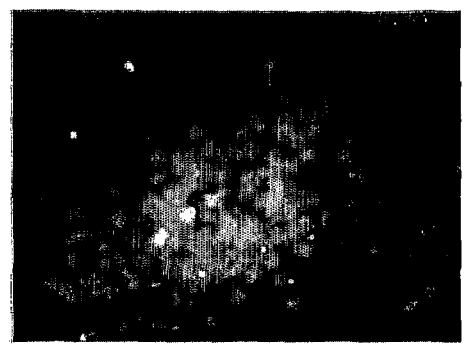
Figure 8E:
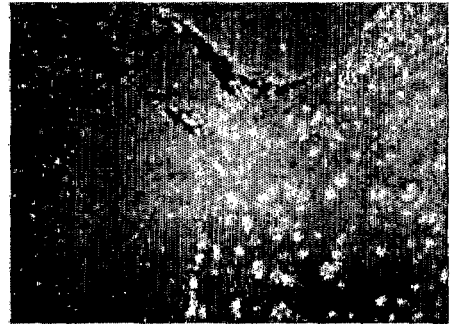
Figure 8F:
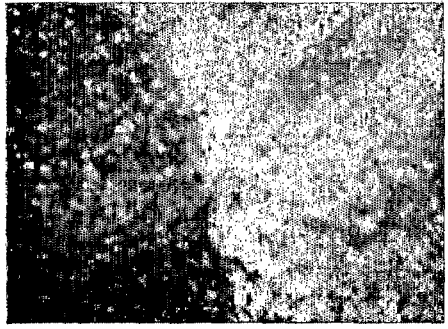

To further examine effects of sulfasalazine in vivo at the cellular level, the tumor sections were examined with commonly used histological markers for cell death, including ApopTag/methyl green (FIGS. 8A and 8B) and terminal deoxynucleotidyl transferase-mediated biotinylated UTP nick end labeling (TUNEL) (FIGS. 8C and 8D), and proliferation (Ki-67) (FIGS. 8E and 8F). Multiple fields from several serial sections from two control group and two treatment group animals (see description above regarding FIG. 7A) were examined. As is typical for WHO grade IV gliomas, control tumors (magnification of 20×) displayed significant tissue necrosis, shown by the brown ApopTag-DAB reaction product (FIG. 8A). Indeed, necrosis is a hallmark of grade IV gliomas and a necessary feature for their histopathological grading as such. At a higher resolution (40×), significant cell death was observed as evident from TUNEL (FIG. 8C) and caspase-3 staining (data not shown). In these figures, TUNEL staining is indicated by a lighter green color against a background of DAPI staining. Interestingly, in corresponding sections from all treatment (sulfasalazine-treated) animals, the tumors showed almost no evidence for necrosis, as shown in a representative section (FIG. 8B), and consistent with that, reduced TUNEL (FIG. 8D) and caspase-3 labeling (data not shown). These sections, however, still showed similar Ki-67 indexes of approximately 15, which are considered to be indicative of high-grade glioma (WHO grade IV) (see FIGS. 8D and 8E). Ki-67 values did not differ significantly in a comparison of 14 representative fields from control group and treatment group animals (data not shown). TUNEL values suggested a lower percentage of apoptotic cells in treatment group (sulfasalazine-treated) versus control group animals, but in a sampling of 21 sections from control and treatment group animals, these values also did not reach statistical significance (data not shown).

Details regarding the methods used in the examples described above can be found in reference (27).

The foregoing description illustrates and describes the methods of the present disclosure. Additionally, the disclosure shows and describes only the preferred embodiments of the methods but, as mentioned above, it is to be understood that the teachings of the present disclosure are capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All references cited herein are incorporated by reference as if fully set forth in this disclosure.

REFERENCES

1. Jefferies H, Coster J, Khalil A, Bot J, McCauley R D, Hall J C (2003) Glutathione. ANZ Journal of Surgery 73: 517-522.
2. Verrey F, Jack D L, Paulsen I T, Saier M H, Jr., Pfeiffer R (1999) New glycoprotein-associated amino acid transporters. J Membr Biol 172: 181-192.
3. Sato H, Tamba M, Ishii T, Bannai S (1999) Cloning and expression of a plasma membrane cystine/glutamate exchange transporter composed of two distinct proteins. J Biol Chem 274: 11455-11458.
4. Bassi M T, Gasol E, Manzoni M, Pineda M, Riboni M, Martin R, Zorzano A, Borsani G, Palacin M (2001) Identification and characterisation of human xCT that co-expresses, with 4F2 heavy chain, the amino acid transport activity system xc-. Pflugers Arch 442: 286-296.
5. Kim J Y, Kanai Y, Chairoungdua A, Cha S H, Matsuo H, Kim D K, Inatomi J, Sawa H, Ida Y, Endou H (2001) Human cystine/glutamate transporter: cDNA cloning and upregulation by oxidative stress in glioma cells. Biochim Biophys Acta 1512: 335-344.
6. Murphy T H, Schnaar R L, Coyle J T (1990) Immature cortical neurons are uniquely sensitive to glutamate toxicity by inhibition of cystine uptake. FASEB J 4: 1624-1633.
7. McBean G J (2002) Cerebral cystine uptake: a tale of two transporters. Trends Pharmacol Sci 23: 299-302.
8. Bender A S, Reichelt W, Norenberg M D (2000) Characterization of cystine uptake in cultured astrocytes. Neurochemistry International 37: 269-276.
9. Patel non-substrate inhibitors of transport system xc-: an obligate exchanger of L-glutamate and L-cystine. Neuropharmacology 46: 273-284.
10. Ye Z C, Sontheimer H (1999) Glioma cells release excitotoxic concentrations of glutamate. Cancer Res 59: 4383-4391.
11. Wu G, Fang Y Z, Yang S, Lupton J R, Turner N D (2004) Glutathione Metabolism and Its Implications for Health. J Nutr 134: 489-492.
12. Louw D F, Bose R, Sima A A, Sutherland G R (1997) Evidence for a high free radical state in low-grade astrocytomas. Neurosurgery 41: 1146-1150.
13. The Children=s Brain Tumor Foundation Internet Site (www/childrensneuronet.org/med/index.html)
14. American Brain Tumor Association Internet Site (www.abta.org)
15. Schoenberg, B. S. (1983). Epidemiology of central nervous system tumor. In: Walker, M D, editor. Oncology of the Nervous System. Boston: Nijhoff; p. 1-30.
16. Levin, A. L., G. E. Shelin, and P. H. Gutin. (1989). Neoplasms of the central nervous system. In: Devita S., Hellman, S., Rosenberg, S. A., editors. Cancer: Principles and Practice of Oncology. 3rd Ed., Philadelphia, Pa.: Lippincott; p. 1557-1611.
17. Kleihues, P., and H. Ohgaki. (1999). Primary and secondary glioblastomas: from concept to clinical diagnosis. Neuro-Oncol. 1:44-51.
18. Danbolt N C (2001) Glutamate uptake. Prog Neurobiol 65: 1-105.
19. Flynn J, McBean G J (2000) Kinetic and pharmacological analysis of -[35S]cystine transport into rat brain synaptosomes. Neurochemistry International 36: 513-521.
20. Ye Z C, Rothstein J D, Sontheimer H (1999) Compromised glutamate transport in human glioma cells: reduction-mislocalization of sodium-dependent glutamate transporters and enhanced activity of cystine-glutamate exchange. J Neurosci 19: 10767-10777.
21. Gout P W, Buckley A R, Simms C R, Bruchovsky N (2001) Sulfasalazine, a potent suppressor of lymphoma growth by inhibition of the x(c)-cystine transporter: a new action for an old drug. Leukemia 15: 1633-1640.
22. Lombardi G, Miglio G, Dianzani C, Mesturini R, Varsaldi F, Chiocchetti A, Dianzani U, Fantozzi R (2004) Glutamate modulation of human lymphocyte growth: in vitro studies. Biochem Biophys Res Commun 318: 496-502.
23. Castro B, Alonso-Varona A, del Olmo M, Bilbao P, Palomares T (2002) Role of gamma-glutamyltranspeptidase on the response of poorly and moderately differentiated rhabdomyosarcoma cell lines to buthionine sulfoximine-induced inhibition of glutathione synthesis. Anticancer Drugs 13: 281-291.
24. Palomares T, Alonso-Varona A, Alvarez A, Castro B, Calle Y, Bilbao P (1997) Interleukin-2 increases intracellular glutathione levels and reverses the growth inhibiting effects of cyclophosphamide on B16 melanoma cells. Clin Exp Metastasis 15: 329-337.
25. Terradez P, Asensi M, Lasso de la Vega M C, Puertes I R, Vina J, Estrela J M (1993) Depletion of tumour glutathione in vivo by buthionine sulphoximine: modulation by the rate of cellular proliferation and inhibition of cancer growth. Biochem J 292: 477-483.

26. Noda T, Iwakiri R, Fujimoto K, Rhoads C A, Aw T Y (2002) Exogenous cysteine and cystine promote cell proliferation in CaCo-2 cells. Cell Prolif 35: 117-129.
27. Chung, W C, Lyons, S A, Nelson, G M, Hamza, H., Gladson, G C L, Gillespie, Y, and Sontheimer, H (2005) Inhibition of Cystine Uptake Disrupts the Growth of Primary Brain Tumors. J. Neuroscience 25: 7101-7110.

What is claimed:

1. A method for treating a glioma, wherein said glioma is dependent on system Xc for uptake of cystine and viability in a subject in need of said treatment, said method comprising administering to said subject a therapeutically effective amount of a N-heterocyclic substituted salicylate compound, where said compound is sulfasalazine, susalimod, disalazine, or salazosulfadimidine, said compound capable of inhibiting cystine uptake by inhibiting system Xc; and administering a radiation therapy.

2. The method of claim 1 where said glioma depends on said system Xc for at least about 85% of cystine uptake.

3. The method of claim 1 where said compound can be administered by routes selected from the group consisting of intravenous, intramuscular, intracranial, transmucosal, transdermal, subcutaneous, intraperitoneal and oral.

4. The method of claim 1 where said glioma is a high-grade glioma.

5. The method of claim 1 where said glioma is selected from the group consisting of: astrocytoma, glioblastoma and medulloblastoma.

6. The method of claim 1 where said inhibition is a direct inhibition.

7. The method of claim 1 where the subject is a human.

8. The method of claim 1 further comprising administering a therapeutically effective amount of a second compound that increases the production of reactive oxygen species in said glioma cell.

9. The method of claim 8 where said second compound is a radioactive compound.

10. The method of claim 8 where said second compound is administered before the administration of said compound capable of inhibiting cystine uptake.

11. The method of claim 8 where said second compound is administered after the administration of said compound capable of inhibiting cystine uptake.

12. The method of claim 8 where said second compound is administered at the same time as the administration of said compound capable of inhibiting cystine uptake.

13. The method of claim 1 where the inhibition of system $X_c^-$ reduces intracellular cystine levels.

* * * * *